United States Patent [19]

Saugues et al.

[11] Patent Number: 5,515,713
[45] Date of Patent: May 14, 1996

[54] PROCESS AND DEVICE FOR DETECTION OF BUBBLES IN A PERFUSION LINE

[75] Inventors: Alain Saugues, Moirans; Marc Brose, Brezins, both of France

[73] Assignee: Becton Dickinson and Company, Franklin Lakes, N.J.

[21] Appl. No.: 286,574

[22] Filed: Aug. 5, 1994

[30] Foreign Application Priority Data

Sep. 30, 1993 [FR] France .................................. 93 11656

[51] Int. Cl.⁶ .......................... G01N 29/00; A61M 31/00
[52] U.S. Cl. .............................. 73/19.03; 73/19.1; 604/65
[58] Field of Search ................................. 73/19.03, 19.1, 73/19.01, 61.71

[56] References Cited

U.S. PATENT DOCUMENTS

| 3,171,273 | 3/1965 | Dijkema | 73/19.1 |
|---|---|---|---|
| 3,182,487 | 5/1965 | Graham | 73/19.1 |
| 3,225,585 | 12/1965 | Wohnoutka | 73/19.1 |
| 3,486,370 | 12/1969 | Chedeville et al. | 73/19.1 |
| 4,068,521 | 1/1978 | Cosentino | 73/19 |
| 4,137,940 | 2/1979 | Faisandier | 137/486 |
| 4,312,341 | 1/1982 | Zissimopoulos | 128/214 |
| 4,496,346 | 1/1985 | Mosteller | 604/123 |
| 4,658,244 | 4/1987 | Meijer | 340/632 |
| 4,668,945 | 5/1987 | Aldrovandi | 340/621 |
| 4,673,927 | 6/1987 | Cianciavicchia | 340/621 |
| 4,751,476 | 6/1988 | Meijer | 331/65 |
| 4,764,166 | 8/1988 | Spani | 604/65 |
| 5,123,275 | 6/1992 | Daoud | 73/19.03 |
| 5,177,993 | 1/1993 | Beckman | 73/19.03 |

*Primary Examiner*—Hezron E. Williams
*Assistant Examiner*—Jay L. Politzer
*Attorney, Agent, or Firm*—Alan W. Fiedler

[57] ABSTRACT

A device and process for detecting a bubble in a perfusion line, i.e., a metering device, using a bubble trap and a bubble detector, wherein the bubble detector detects substantially large bubbles that may flow through the bubble trap if the bubble trap or fluid source fails.

4 Claims, 6 Drawing Sheets

PROCESS AND DEVICE FOR DETECTION OF BUBBLES IN A PERFUSION LINE

The present invention deals in general with the area of bubble detection in fluid piping systems. It is more particularly concerned with a bubble detector for a medical perfusion system.

During medical treatment, fluids are often perfused into the bodies of patients with metering pumps and syringe pumps. These pumps are connected to the patient by means of a flexible casing. During perfusion, it is possible that air bubbles may form in the casing. The formation of air bubbles is undesirable and may cause injury to the patient. The bubbles may be large or extremely small in size (called "micro-bubbles").

In the prior art, bubbles have been detected by means of ultrasonic, optical, and compression devices. These devices are used to trigger alarms or to end a perfusion if bubbles are detected. The detection of micro-bubbles by this process is difficult and costly. If the device must detect bubbles of small size, a large number of false alarms may occur. If the device detects only bubbles of large size, false alarms can be reduced, but at the risk of perfusion of micro-bubbles. A single micro-bubble entails little risk of damage. However, it is known that a large number of micro-bubbles perfused into the body of a patient over a period of time produces damage.

A metering perfusion pump must be applied to detect a bubble with a volume of approximately 0.05 ml or less. By using detectors of the prior art, an alarm is triggered only after a determination that the bubble volume exceeds a critical volume. The time required to reach this critical volume depends on the flow rate. This process thus contributes to the generation of false alarms and is characterized by a slow detection of bubbles.

Air bubbles can be imprisoned in a chamber disposed in the perfusion line. However, such a trap must be sized to ensure that it will be suitable to receive bubbles forming over a prolonged period of time. As a result, the volume of the perfusion line is increased, characterized by a longer priming time and a loss of the drug.

The present invention concerns a device for the detection of bubbles in a perfusion line, e.g., in a metering pump. A first tube is designed to transport a fluid. A bubble trap is connected to the first tube. The bubble trap has an intake connected to the first tube, a chamber that can be filled with the fluid, and an outlet. When a bubble penetrates into the chamber through the intake, an equivalent volume of fluid is moved from the chamber and leaves the receptacle through the outlet. A second tube is connected to the outlet of the receptacle. The second tube crosses a bubble detector to detect a bubble in the second tube. Means are provided to generate a signal if a bubble is detected by the bubble detector.

The present invention is also concerned with a process for the detection of bubbles in a fluid in a tube. The process comprises steps consisting of providing a first tube and a second tube; of providing a bubble trap having an intake connected to the first tube and an outlet connected to the second tube; of priming the receptacle with fluid; of providing a bubble detector in such a manner that the bubble detector can detect a gas in the second tube; of causing the fluid to flow into the bubble trap from the first tube and out of the bubble trap through the outlet so that a bubble in the fluid in the first tube moves an equivalent volume of the fluid in the bubble trap as it enters the receptacle; of permitting the bubble trap to be essentially evacuated of fluid so that the bubble trap is essentially filled with gas in such a way that a portion of the gas leaves the bubble trap through the outlet and penetrates into the second tube; of detecting the quantity of gas in the second tube; and of generating a signal after detection of the quantity of gas in the second tube.

In order to better understand the invention, a nonlimiting exemplified embodiment is described below, referring to the annexed drawings, on which:

Figure 3A:
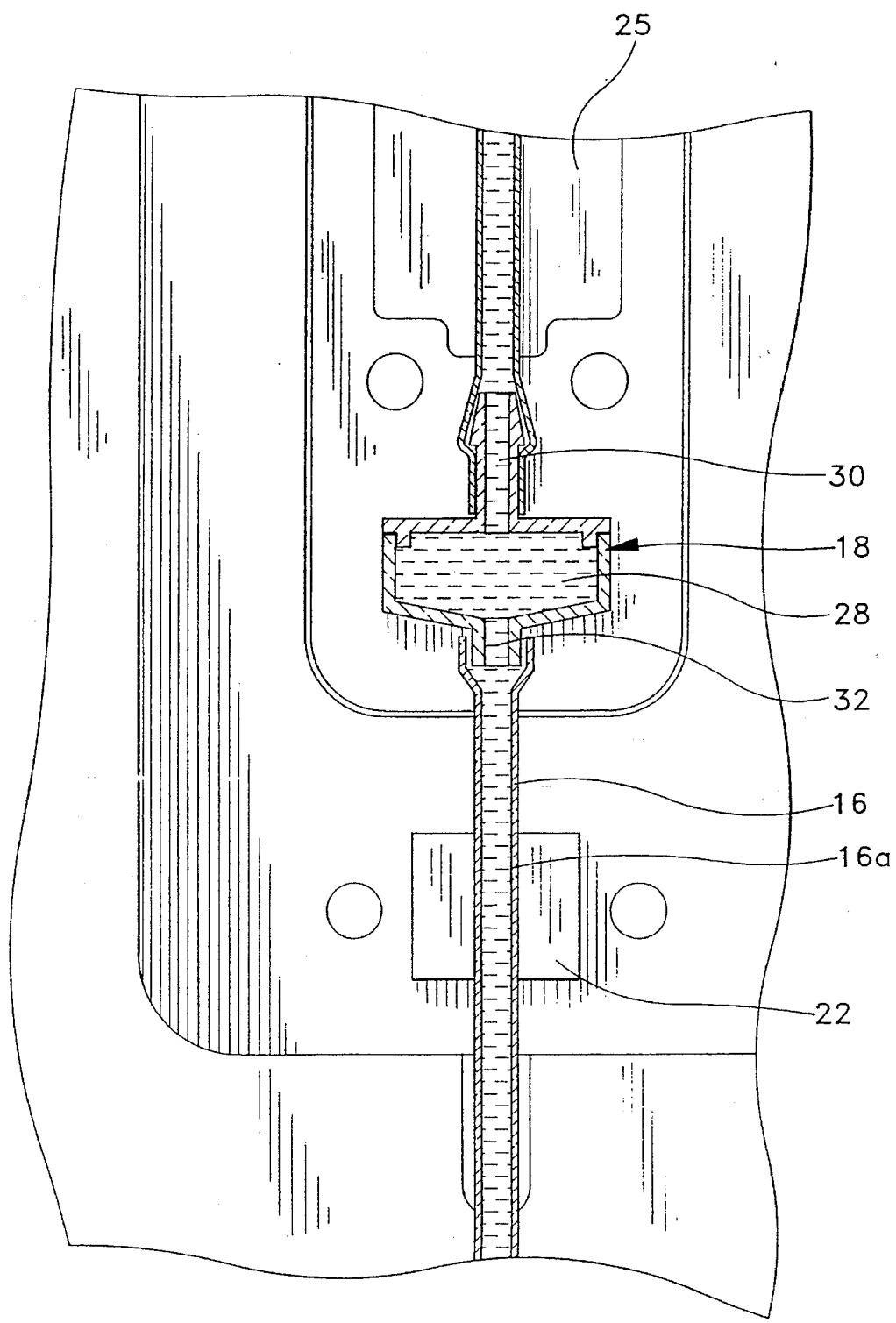
Figure 4:
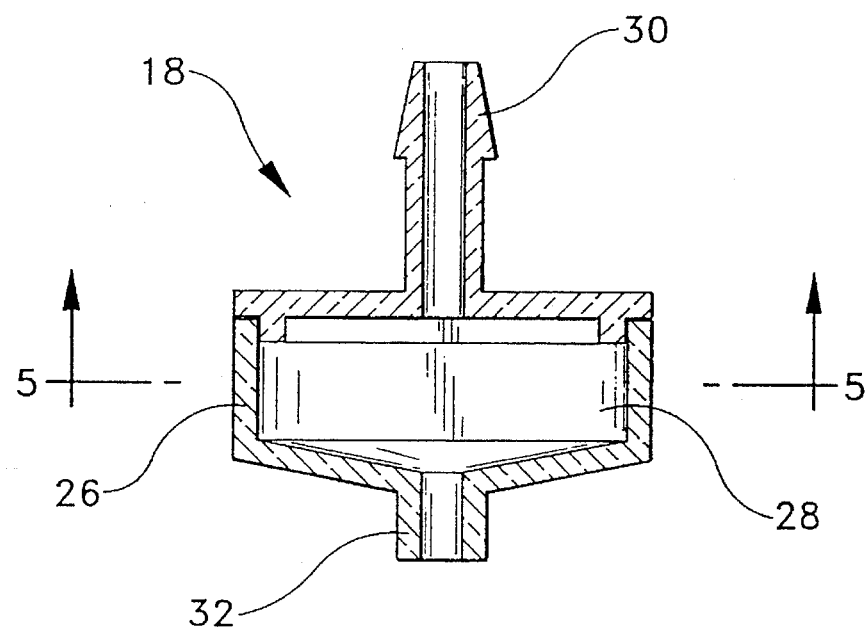
Figure 5:
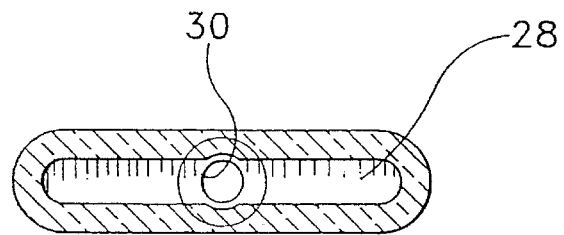

FIGS. 3a, b, and c are detailed elevations representing the operation of the invention;

FIG. 4 is a detailed view of the bubble trap according to the invention;

FIG. 5 is an overhead view of the bubble trap according to the invention.

Figure 1:
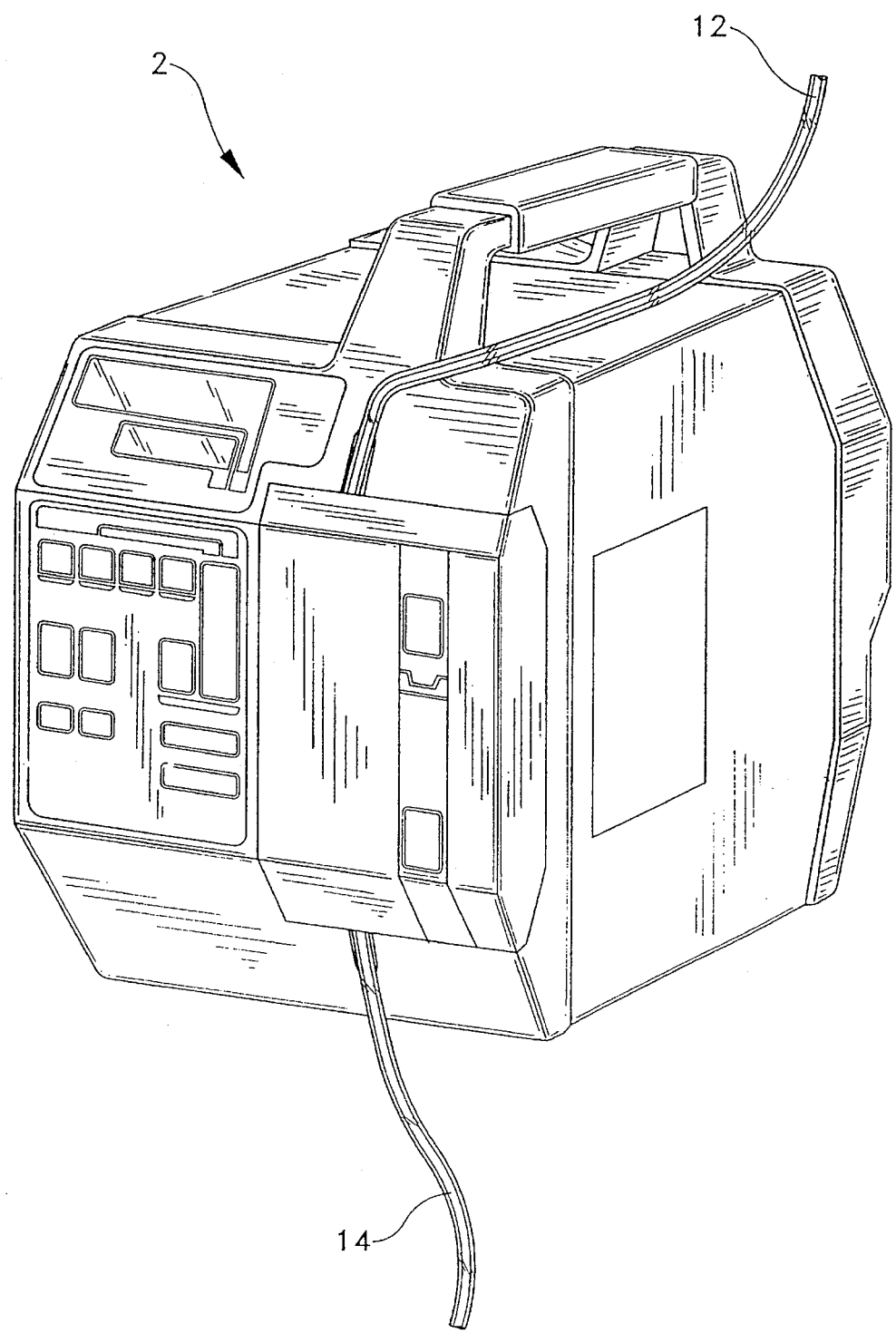
FIG. 1 is a perspective view of a metering pump incorporating the present invention.
Figure 2:
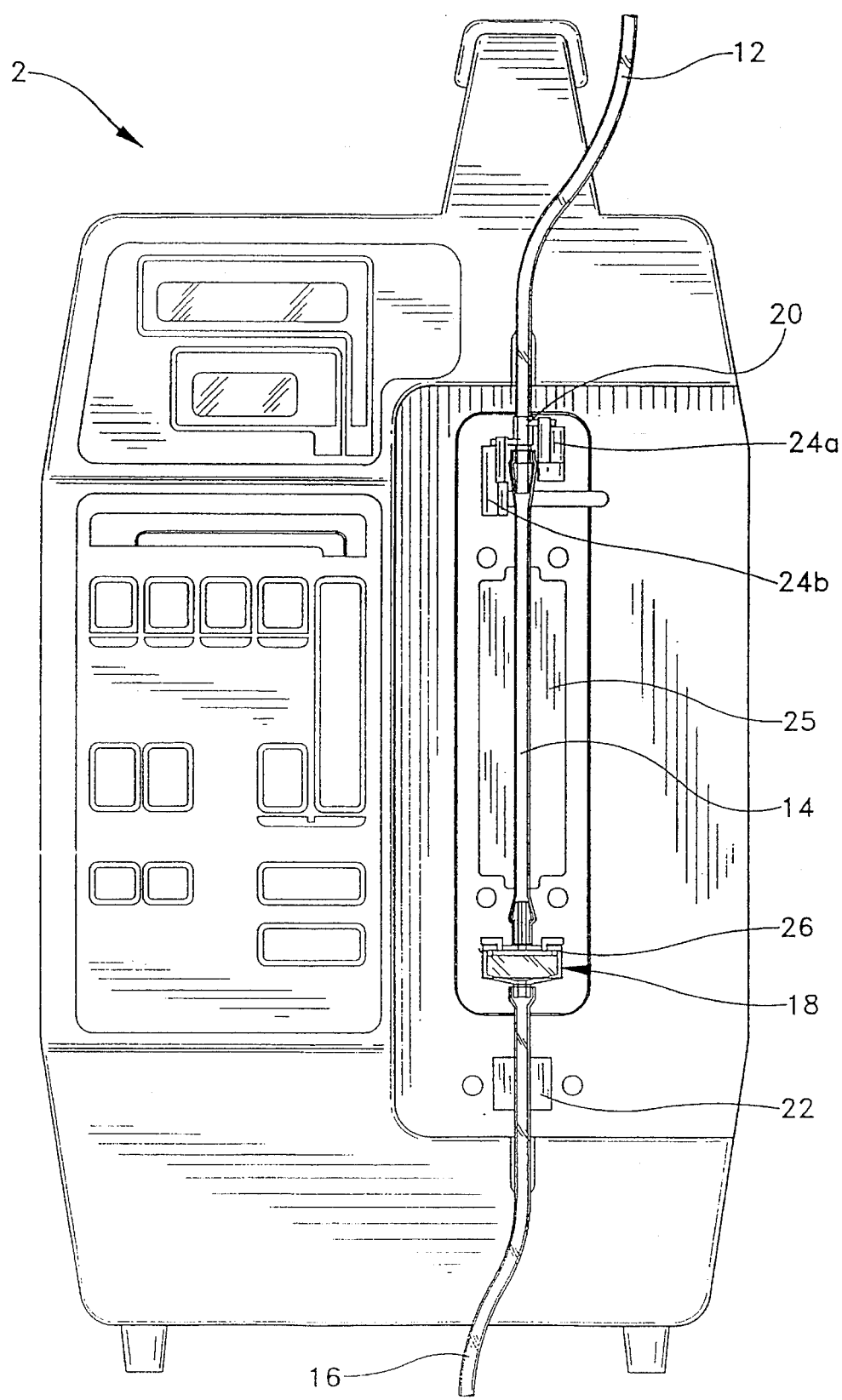
FIG. 2 is a detailed elevation of the casing and of the detection system of the invention.

FIG. 1 represents a metering pump 2 incorporating the present invention. Such a pump is available from Becton Dickinson Infusion Systems of Brezins, France under the name "VIP II". The invention is represented in greater detail in FIG. 2. The bubble detector is made up of the bubble trap 18 in series with the detector 22. The tube 12 is connected to a reservoir of fluid which is to be perfused into the body of a patient (not shown). Tube 12 is part of a modified, commercially available perfusion kit designed to receive pump VIP II and available from Becton Dickinson Infusion Systems. A positioning element 20 is connected to tube 12 and acts to position tube 12 precisely in pump 2. Pump 2 is equipped with tabs 24a and 24b which hold tube 12 in position on pump 2 so that it will not be installed backwards or upside down. Tube 12 is typically made of PVC. Attached to tube 12 is tube 14 which is typically made of silicone rubber. The flexibility of silicone rubber makes it quite appropriate for application in metering pumps which use the action of a cam or of a peristaltic device resting on tube 14 to pump the fluid from the reservoir. Pump VIP II represented on FIGS. 1 to 5 has such a device 25.

Tube 14 is attached to a bubble trap 18 which consists of a receptacle 26 with a chamber 28. The fluid can flow from tube 14 into chamber 28 through an intake 30 which is connected to tube 14 (cf. FIG. 3a). The fluid can escape from chamber 28 through outlet 32 which is connected to tube 16. Tube 16 is in turn connected to a catheter or similar device which can be inserted in the blood vessel of a patient for a fluid perfusion.

In the preferred exemplified embodiment, the volume of chamber 28 ranges between approximately 0.2 and 0.3 ml. The internal diameter of the casing is approximately 3 mm.

Tube 16 crosses bubble detector 22, which is an inexpensive bubble detector well known in the trade. Preference is given to an ultrasonic bubble detector. Any currently available bubble detector can be used, provided that it is qualified to detect a bubble with a volume of approximately 0.1 ml for the preferred configuration described above. Such a bubble will occupy approximately 15 mm of the casing. The detector 22 generates a signal which interrupts the operation of the pump 2 when a bubble is detected. The detector is preferably calibrated to detect bubbles of a volume substantially greater than without the bubble trap.

Figure 3B:
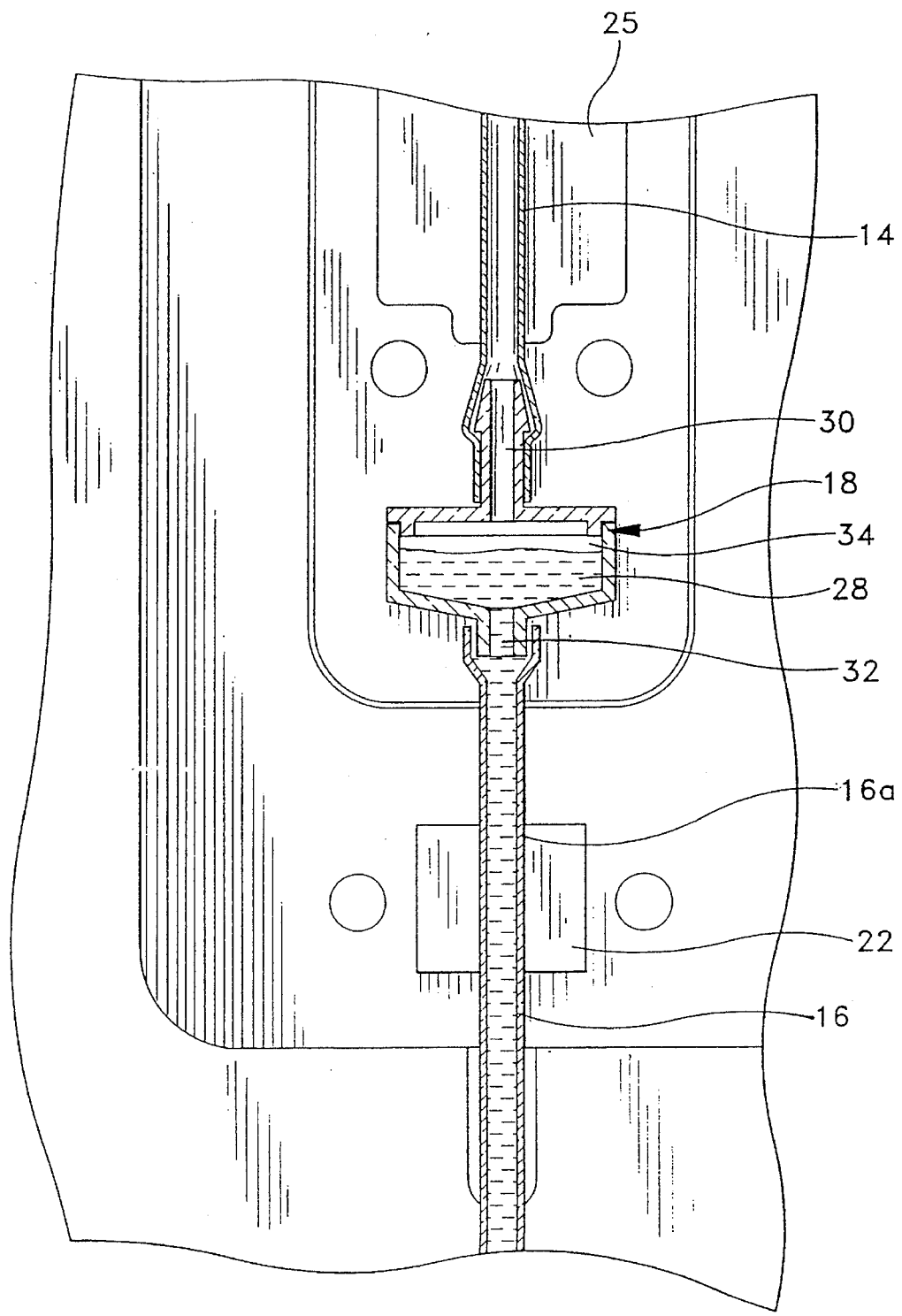
Figure 3C:
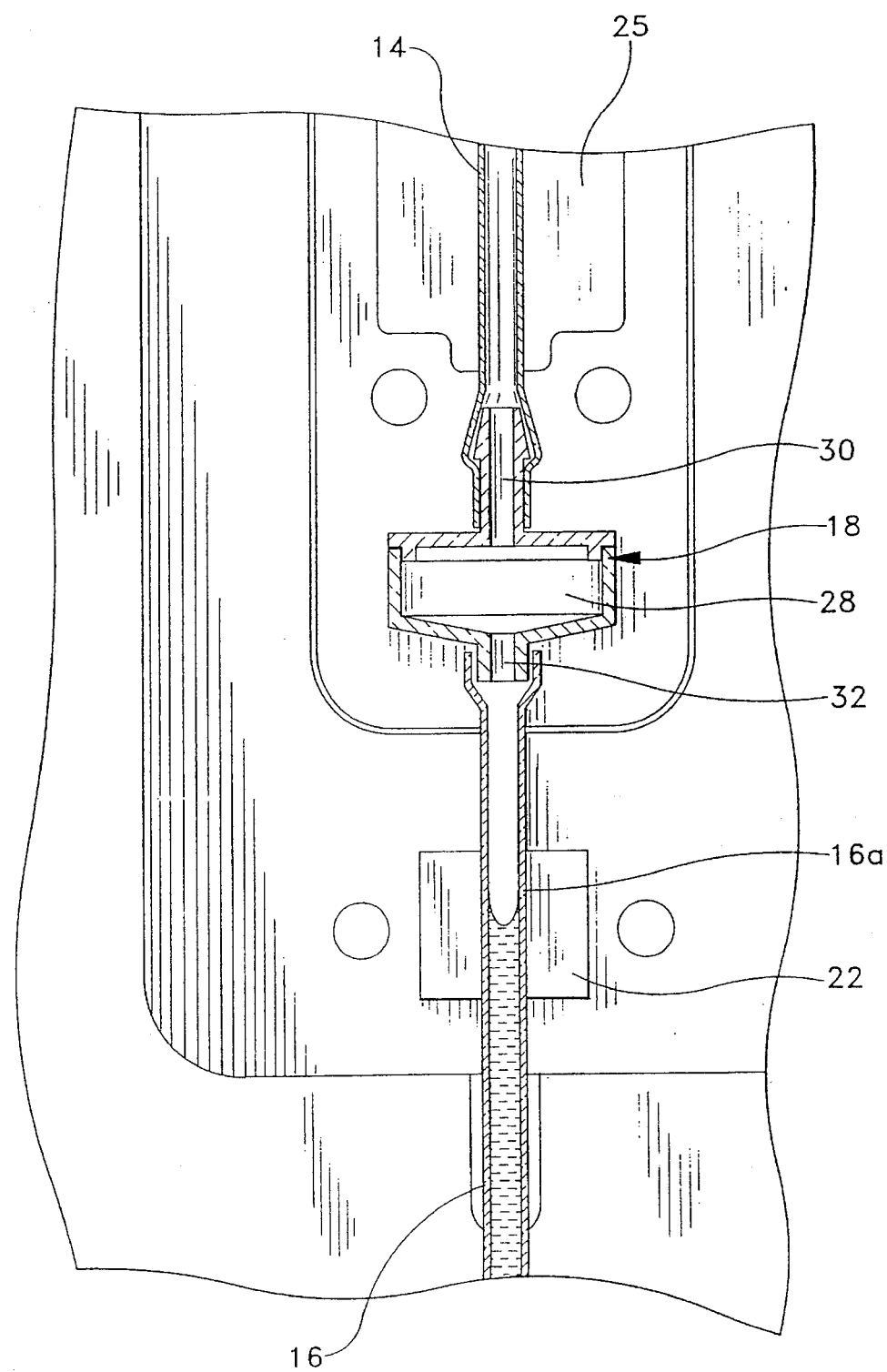

When the pump 2 is put in place for use, the fluid piping system made up of tubes 12, 14, and 16 is primed with the fluid to be perfused. The chamber 28 is also primed with the fluid. When pump 2 pumps the fluid, the fluid crosses the casing. As long as the fluid is pumped, the chamber 28 remains full of fluid. If air or another gas 34 in the form of a bubble is present in the fluid, it penetrates into chamber 28. Cf. FIG. 3b. Since air or a gas is less dense than the fluid, it will not be pumped from chamber 28 into tube 16. On the contrary, the air or the gas will displace an equivalent volume of fluid and will be imprisoned in chamber 28. When more bubbles penetrate into chamber 28, the fluid in chamber 28 will be displaced. Cf. FIG. 3c. Eventually, if numerous bubbles are displaced into chamber 28, practically all of the fluid will be displaced and only the air or the gas coming from the bubbles will still be present. Another pumping will cause at least one displacement of the air or of the gas toward the bottom of tube 16 and into the region 16a which is aligned on the bubble detector 22. When this happens, the bubble detector 22 will generate a signal which can be used to stop the pump 2 before the bubble penetrates into the body of the patient.

The bubble trap 18 will imprison bubbles of any size. As a result, even micro-bubbles will be prevented from penetrating into the tube 16 and consequently into the body of the patient. The bubble detector 22 can be a relatively inexpensive bubble detector capable of detecting bubbles of relatively large dimensions. It suffices that it be triggered when bubbles of large dimensions are present, since it is required to operate when the fluid has been evacuated from chamber 28 and a large-sized bubble is pushed into the tube 16. Thanks to the present invention, and in particular to low flow rates resulting from the absence of micro-bubbles, the alarm can be triggered immediately when a bubble is detected without the calculation of the critical volume necessary with systems in the prior art. However, the relatively small volume of the trap permits the pump to generate alarms for low volumes of air in the piping.

We claim:

1. Device for detecting bubbles in a perfusion fine comprising:

a first robe to trampon a fluid;

a bubble trap comprising:

an intake connected to the first robe for receiving the fluid, a receptacle connected to the intake and having a chamber which can be filled with the fluid from the intake, and an outlet connected to the receptacle for dispensing the fluid from the receptacle, the outlet being at an elevation below that of the intake;

a second tube connected to the outlet of the bubble trap to transport the fluid;

a bubble detector to detect a bubble in the second tube, the bubble detector being positioned downstream from the bubble trap and at an elevation below that of the bubble trap so that the fluid can flow from the bubble trap into the bubble detector; and means to generate a signal if a bubble is detected by the bubble detector.

2. Device according to claim 1, wherein the bubble detector is calibrated to detect bubbles having a volume greater than approximately 0.1 ml.

3. Process for the detection of bubbles in a fluid in a tube, wherein the bubbles are composed of a gas, the process comprising the steps of:

providing a first tube and a second tube;

providing a bubble trap having an intake connected to the first tube, an outlet connected to the second tube, and a receptacle;

providing a bubble detector connected to the second tube to detect a gas in the second tube;

causing fluid to flow into the bubble trap from the first tube and out of the bubble trap through the outlet and into the second tube;

permitting the bubble trap to be virtually evacuated of liquid so that the bubble trap is essentially filled with gas thereby causing a portion of the gas to leave the bubble trap through the outlet and enter the second tube; and detecting the portion of the gas in the second tube using the bubble detector and generating a signal upon detection of the portion of gas in the second tube.

4. Process according to claim 3, wherein the detection step is accomplished by a bubble detector able to detect a bubble having a volume greater than approximately 0.1 ml.

\* \* \* \* \*